(12) United States Patent
Cowan et al.

(10) Patent No.: US 9,101,713 B2
(45) Date of Patent: Aug. 11, 2015

(54) CONSTANT FORCE SYRINGE

(71) Applicant: MEDRAD, INC., Indianola, PA (US)

(72) Inventors: Kevin P. Cowan, Allison Park, PA (US); Barry L. Tucker, Verona, PA (US)

(73) Assignee: Bayer Medical Care Inc., Indianola, PA (US)

( * ) Notice: Subject to any disclaimer, the term of this patent is extended or adjusted under 35 U.S.C. 154(b) by 0 days.

(21) Appl. No.: 13/797,959

(22) Filed: Mar. 12, 2013

(65) Prior Publication Data

US 2014/0276451 A1    Sep. 18, 2014

(51) Int. Cl.
| | |
|---|---|
| *A61M 5/315* | (2006.01) |
| *A61M 5/168* | (2006.01) |
| *A61M 5/20* | (2006.01) |
| *A61M 5/00* | (2006.01) |
| *A61M 5/145* | (2006.01) |

(52) U.S. Cl.
CPC ............ *A61M 5/16877* (2013.01); *A61M 5/007* (2013.01); *A61M 5/14526* (2013.01); *A61M 5/2053* (2013.01); *A61M 5/31515* (2013.01)

(58) Field of Classification Search
CPC ...................... A61M 5/31511; A61M 5/14526; A61M 5/48; A61M 5/16877; A61M 5/2053
USPC .......... 604/118.187, 226, 121, 125, 207, 218, 604/246, 187, 214, 221, 222
See application file for complete search history.

(56) References Cited

U.S. PATENT DOCUMENTS

| | | |
|---|---|---|
| 4,006,736 A | 2/1977 | Kranys et al. |
| 4,677,980 A | 7/1987 | Reilly et al. |
| 5,176,642 A | 1/1993 | Clement |
| 5,383,858 A | 1/1995 | Reilly et al. |
| 5,494,036 A | 2/1996 | Uber, III et al. |

(Continued)

FOREIGN PATENT DOCUMENTS

WO    0192907 A2    6/2001

OTHER PUBLICATIONS

"A Primer on Medical Device Interactions with magnetic Resonance Imaging Systems," accessed at http://www.fda.gov/cdrh/ode/primerf6.html, accessed on Sep. 5, 2007, pp. 15.

(Continued)

*Primary Examiner* — Jason Flick
*Assistant Examiner* — Leah Stohr
(74) *Attorney, Agent, or Firm* — Joseph L. Kent; David Schramm; James R. Stevenson

(57) ABSTRACT

Various syringe systems are disclosed. One such syringe system may include a body having a hollow lumen and a distal end, a vacuum chamber disposed within the hollow lumen of the syringe body, a first plunger connected to a distal portion of the vacuum chamber, the first plunger forming a first seal against an inner surface of the syringe body and defining a fluid delivery volume between the first plunger and the distal end of the syringe body, a second plunger disposed within the vacuum chamber, the second plunger forming a second seal against an inner surface of the vacuum chamber and defining a proximal and distal volume compartments within the vacuum chamber, and a piston affixed to the second plunger, the piston configured to move the second plunger within the vacuum chamber, thereby altering a volume of the proximal volume compartment and a volume of the distal volume compartment.

17 Claims, 5 Drawing Sheets

(56) References Cited

U.S. PATENT DOCUMENTS

| | | |
|---|---|---|
| 5,588,556 A | 12/1996 | Sancoff et al. |
| 5,746,208 A | 5/1998 | Prince |
| 5,769,824 A * | 6/1998 | Hjertman et al. ............. 604/143 |
| RE37,602 E | 3/2002 | Uber, III et al. |
| 6,387,228 B1 | 5/2002 | Maget |
| 6,413,238 B1 | 7/2002 | Maget |
| 6,425,885 B1 * | 7/2002 | Fischer et al. ................ 604/218 |
| 6,704,592 B1 | 3/2004 | Reynolds et al. |
| 7,221,159 B2 | 5/2007 | Griffiths et al. |
| 7,283,860 B2 | 10/2007 | Frazier et al. |
| 7,315,109 B1 | 1/2008 | Griffiths et al. |
| 7,632,245 B1 | 12/2009 | Cowan et al. |
| 2002/0115933 A1 | 8/2002 | Duchon et al. |
| 2004/0030233 A1 | 2/2004 | Frazier et al. |

OTHER PUBLICATIONS

Keeler, E.K., et al., "Accessory Equipment Considerations with Respect to MRI Compatibility," JMRI, vol. 8, No. 1, pp. 12-18 (1998).

Lemieus, L., et al. "Recording of EEG during fMRI experiments: patient safety," Magnetic Resonance in Medicine, vol. 38, No. 6, pp. 943-952, John Wiley & Sons, Inc. (1997).

The International Search Report and Written Opinion mailed Jul. 8, 2014 of corresponding PCT Application No. PCT/US2014/023214.

\* cited by examiner

CONSTANT FORCE SYRINGE

BACKGROUND

During various medical procedures, it may be necessary to administer medications, supplements, fluids, contrast media, saline, and/or the like to a patient. In general, administration may occur subcutaneously, intramuscularly, intraperitoneally, and/or intravenously. In some instances, administration may be accomplished with the use of a manually activated syringe.

Occasionally, a constant rate of administration may be of particular concern to the medical services provider and/or the patient. In an illustrative example, biological cells included in some treatments may be susceptible to damage if the pressure and/or the flow rate of the injection is too high. Furthermore, damage to the biological cells may reduce the efficacy of treatment. In another illustrative example, the rate of delivery may be important to ensure proper uptake of an agent. Even the most skilled medical services provider may struggle with the process of smoothly administering at a constant rate.

Previous attempts to ensure smooth administration of medications, supplements, fluids, contrast media, and/or the like at a constant rate have resulted in injector systems that are used to administer a fluid at a constant rate that are complicated and expensive to use and implement.

SUMMARY

In an embodiment, a syringe system may include a syringe body having a hollow lumen and a distal end, the syringe body being configured to house a fluid therein, a vacuum chamber disposed within the hollow lumen of the syringe body, a first plunger connected to a distal portion of the vacuum chamber within the hollow lumen of the syringe body, the first plunger forming a first seal against an inner surface of the syringe body and defining a fluid delivery volume between the first plunger and the distal end of the syringe body, a second plunger disposed within the vacuum chamber, the second plunger forming a second seal against an inner surface of the vacuum chamber and defining a proximal volume compartment and a distal volume compartment within the vacuum chamber, and a piston affixed to the second plunger and extending proximally out of the vacuum chamber, the piston configured to move the second plunger within the vacuum chamber, thereby altering a volume of the proximal volume compartment and a volume of the distal volume compartment.

In an embodiment, a syringe system may include a syringe body having a hollow lumen and a distal end, the syringe body being configured to house a fluid therein, a vacuum chamber at least partially disposed within the hollow lumen of the syringe body, a first plunger disposed distally to the vacuum chamber within the hollow lumen of the syringe body, the first plunger forming a seal against an inner surface of the syringe body and defining a fluid delivery volume between the first plunger and the distal end of the syringe body, a second plunger disposed within the vacuum chamber, the second plunger defining a proximal volume compartment and a distal volume compartment within the vacuum chamber, and a piston extending distally out of the vacuum chamber and connected to the first plunger and the second plunger, the piston configured to move the second plunger within the vacuum chamber and the first plunger within the syringe body.

In an embodiment, a syringe system may include a syringe body having a hollow lumen and a distal end having a tip, the syringe body being configured to house a fluid therein, a vacuum chamber at least partially disposed within the hollow lumen of the syringe body, a first plunger disposed distally to the vacuum chamber within the hollow lumen of the syringe body, the first plunger forming a seal against an inner surface of the syringe body and defining a fluid delivery volume between the first plunger and the distal end of the syringe body, a second plunger disposed within the vacuum chamber, the second plunger defining a proximal volume compartment and a distal volume compartment within the vacuum chamber, a piston extending distally out of the vacuum chamber and connected to the first plunger and the second plunger, the piston configured to move the second plunger within the vacuum chamber and the first plunger within the syringe body, and a thumb piece removably attached to a proximal portion of the vacuum chamber. The thumb piece may be configured to provide a surface for a user to apply a force in a substantially distal direction. The thumb piece may be further configured to increase and decrease a volume of the proximal volume compartment.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the figures. However, embodiments may assume alternative variations and step sequences, except where expressly specified to the contrary. The specific devices and processes illustrated in the attached drawings and described in the following specification, are exemplary embodiments. Hence, physical characteristics related to the embodiments disclosed herein are not to be considered as limiting.

The word "proximal" refers to a direction relatively closer to a clinician or operator using the device described herein, and the word "distal" refers to a direction relatively further from the clinician or operator. For example, the end of a syringe placed nearest the body of a patient is considered a distal end of the syringe, while the end closes to the clinician is a proximal end of the syringe. The terms "axial" or "axially" refer generally to an axis around which the particular objects being referred to are preferably formed (although not necessarily symmetrically therearound). The term "radial" refers generally to a direction normal to the axis or along a radius of an object having a circular cross-section.

Various embodiments of the present disclosure may be directed to syringes, particularly those used for manual fluid delivery, that may rely on a transient vacuum induced within one or more compartments of the syringe. In some embodiments, the fluid may be delivered from the syringe at a uniform rate because the vacuum itself powers the fluid delivery instead of the person or device pressing on the thumb piece of the syringe.

Figure 1A:
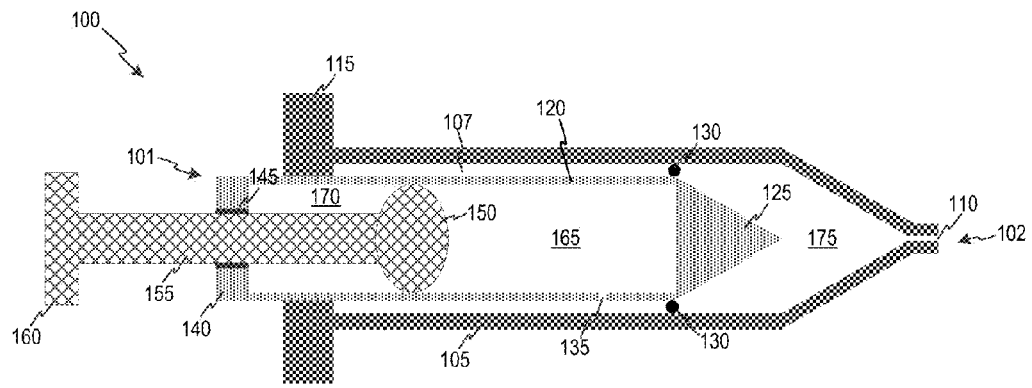
FIG. 1A depicts a side view of a syringe having a vent according to an embodiment.

FIG. 1A depicts a side view of a syringe, generally designated 100, having a vent 135 according to an embodiment. The syringe 100 may generally include a syringe body 105 having a hollow lumen 107, a proximal end 101, and a distal end 102 having a tip 110. The syringe body 105 is not limited in shape or size by this disclosure, and may be any shape or size, particularly shapes and sizes of syringe bodies commonly known by those skilled in the art. In various embodiments, the syringe body 105 may be substantially cylindrical. In various embodiments, the syringe body 105 may be about 4 ml to about 20 ml in volume. In particular embodiments, the volume of the syringe body 105 may be about 4 ml, about 5 ml, about 10 ml, about 15 ml, about 20 ml, or any value or range between any two of these values. In various embodiments, the syringe 100 may be made of glass, a polymer, and/or the like.

In various embodiments, the hollow lumen 107 may include a plurality of plungers disposed therein. For example, in the present embodiment, the hollow lumen 107 may have a first plunger 125 and a second plunger 150. However, those skilled in the art will recognize that more than two plungers may be used without departing from the scope of this disclosure. In some embodiments, a vacuum chamber 120 may be disposed within the syringe body 105 in contact with the first plunger 125. In various embodiments, the first plunger 125 may form a seal against the interior of the syringe body 105 by means of a first seal 130. In some embodiments, the first seal 130 may be a separate component from the first plunger 125, such as, for example, an added O-ring and/or the like. In these embodiments, the first seal 130 may be fixedly attached to the first plunger 125 by any means of attachment, including attachment apparatuses, adhesives, and/or the like, or the first seal may removably attached to the first plunger. In other embodiments, the first seal 130 may be fabricated as a portion of the first plunger 125. In some embodiments, the first seal 130 may be associated with a distal portion of the vacuum chamber 120.

In various embodiments, the second plunger 150 may be disposed within the vacuum chamber 120. In some embodiments, the second plunger 150 may be mechanically activated by a piston 155. The second plunger 150 may be attached to the piston 155 by any means of attachment, including, but not limited to, any number of clips, fasteners, hooks, adhesives, and/or the like. In some embodiments, the second plunger 150 may be molded as a portion of the piston 155. In some embodiments, the piston 155 may at least partially extend out of an opening of the proximal end 101 of the syringe body 105. In some embodiments, the piston 155 may generally extend out of the vacuum chamber 120 through a proximal wall 140. The opening in the proximal wall 140 may be sealed with a second seal 145 to the piston 155. The second seal 145 may be an air-tight seal around the shaft of the piston 155. In some embodiments, in lieu of the vent 135, the piston 155 may contain a bore therethrough, such as 180 in FIG. 1B or 180' in FIG. 1C, as described in greater detail herein.

In various embodiments, a proximal portion of the piston 155 may be connected to a thumb piece 160. The thumb piece 160 may generally provide a surface upon which a user's digits or another device applies a force to move the piston 155 in either a distal or proximal direction. The thumb piece 160 depicted herein is a generally flat surface; however, those skilled in the art will recognize that the shape and size of the thumb piece is not limited by this disclosure, and may include any number of rings, openings, contoured surfaces, and/or the like without departing from the scope of the present disclosure. Persons skilled in the art will also note that the term 'thumb piece' is not intended to be limiting; while a thumb may be a preferred digit for manipulating the thumb piece 160, the user may use any object to manipulate the thumb piece as described herein. In an illustrative example, a user may press his/her thumb against the thumb piece 160 to effect distal movement of the piston 155 and/or other components of the syringe 100, as described in greater detail herein.

Similar to the first plunger 125 described herein, in various embodiments, the second plunger 150 may form an airtight seal against an interior surface of the vacuum chamber 120, thereby dividing the vacuum chamber into two volume compartments. A distal volume compartment 165 may be created by the space between a distal surface of the second plunger 150 and a proximal end of the first plunger 125. A proximal volume compartment 170 may be created by the space between a proximal surface of the second plunger 150 and a distal surface of the proximal wall 140 of the vacuum chamber 120.

In various embodiments, the vacuum chamber 120 may be detachable from the first plunger 125. The ability to detach the vacuum chamber 120 from the first plunger 125 may allow for use of vacuum chambers that vary in size and shape, thereby increasing compatibility with a wide range of forces to allow for varying pressures and flow rates, as described in greater detail herein.

In various embodiments, the vacuum chamber 120 may include a vent 135. The vent 135 may generally be an opening within the vacuum chamber to allow fluid communication of air between the distal volume compartment 165 and an area outside the syringe body 105. In some embodiments, the communication between the vent 135 and the area outside the syringe body 105 may be along a path bounded by the inner surface of the syringe body and the outer surface of the vacuum chamber 120.

In various embodiments, a fluid delivery volume 175 may be defined within the syringe body 105. In some embodiments, the fluid delivery volume 175 may be defined as the space that is located distally to the first plunger 125. In some embodiments, the fluid delivery volume 175 may contain a fluid therein. Examples of fluids are not limited by this disclosure, and may include, for example, medications, supplements, bodily fluids, contrast media, saline, and/or the like. In some embodiments, fluid contained within the fluid delivery volume 175 may be delivered through the tip 110. The tip 110 may further be configured to be connected to additional elements, such as, for example, needles, tubes, nozzles, and/or the like for delivery of the fluid. It may be appreciated that the first seal 130 may be configured to prevent air transfer from either outside the syringe body 105 or the vacuum chamber 165 from entering the delivery volume 175. Similarly, the first seal 130 may be configured to prevent air and/or fluid from escaping the delivery volume 175 into the vacuum chamber 165 and/or the remainder of the syringe body 105. The volume of the delivery volume 175 may be determined by the distance between the first plunger 125 and the distal end 102 of the syringe body 105, as well as the circumference of the syringe body.

In various embodiments, one or more finger guards 115 may be positioned at a location that is generally located at or near the proximal end 101 of the syringe body 105. In some embodiments, the finger guards 115 may generally be located on an outside surface of the syringe body 105 and may generally extend from the outside surface of the syringe body. In some embodiments, the finger guards 115 may act to provide stability to the syringe 100 during operation. In some embodiments, a user may use the finger guards 115 to prevent movement of the syringe 100 during operation. In some embodiments, the user may use the finger guards 115 to prevent the syringe 100 from slipping out of the user's hand. In some embodiments, the user may use the finger guards 115 to protect the user's fingers. In some embodiments, the finger guards 115 may act as a stopping device to prevent the piston 155 from moving further distally inside the syringe body 105. The shape and size of the finger guards 115 are not limited by this disclosure, and may be any shape and/or size known in the art. Specific examples of shapes may be ring shaped, wedge shaped, and/or the like.

Figure 1B:
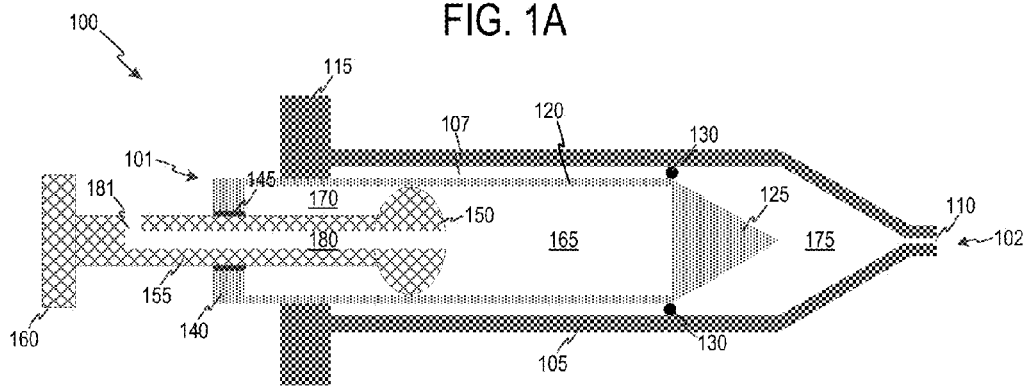
FIG. 1B depicts a side view of a syringe having an angled bore according to an embodiment.
Figure 1C:
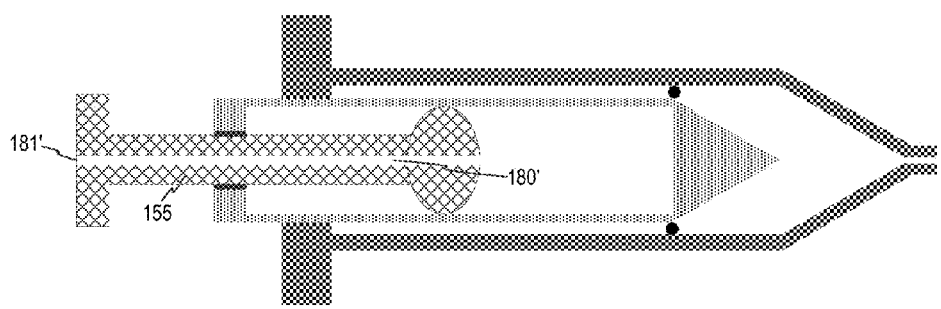
FIG. 1C depicts a side view of a syringe having a bore that extends through the thumb piece according to an embodiment.

In various embodiments, as depicted in FIGS. 1B and 1C, the bore 180, 180' may be used in lieu of the vent 135 (FIG. 1A). In some embodiments, the bore 180, 180' may extend through at least a portion of the piston 155 and/or the second plunger 150. In some embodiments, the bore 180, 180' may be configured to allow air from outside the syringe 100 to enter and/or escape the vacuum chamber 120, effectively regulating by increasing and/or decreasing the pressure of air inside the vacuum chamber. In some embodiments, the bore 180 may include a bore outlet 181 containing a valve and/or the like to assist in regulation of air pressure inside the vacuum chamber 120. In some embodiments, the valve may be incorporated within the thumb piece 160. In other embodiments, the valve may be a separate element, such as a one way check valve or the like. In yet other embodiments, a user may use his/her finger to block the bore 180 in a manner similar to that of a valve. In some embodiments, such as the syringe shown in FIG. 1B, the bore 180 may be curved or angled so that the bore outlet 181 is located substantially on a side of the piston 155, such as, for example, a top side, a bottom side, or the like. In other embodiments, such as the syringe shown in FIG. 1C, the bore 180' may be substantially straight and/or linear with the piston 155. Such a configuration may allow for the bore outlet 181' to be located at or near the thumb piece 160. In some embodiments with this configuration, the thumb piece 160 may act as the valve to block the bore outlet 181', as previously described herein. In other embodiments with this configuration, a user may block the bore outlet 181' with an external apparatus, a thumb, and/or the like while manipulating the thumb piece 160 at the same time.

Figure 2A:
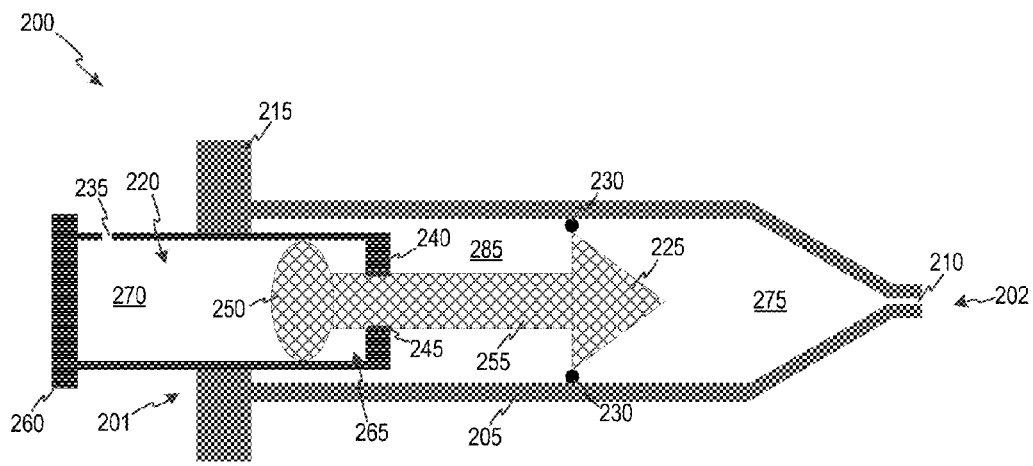
FIG. 2A depicts a side view of an alternative syringe having a side vent according to an embodiment.

FIG. 2A depicts a side view of an alternative syringe, generally designated 200, according to an embodiment. Similar to the syringe 100 disclosed with respect to FIGS. 1A-1C above, the syringe 200 may include a syringe body 205 having a proximal end 201 and a distal end 202. In some embodiments, the syringe body 205 may include a first plunger 225 disposed therein, the plunger incorporating a first seal 230, as previously described herein. A delivery volume 275 may be formed between the distal surface of the first plunger 225 and the tip, as previously described herein.

In various embodiments, a vacuum chamber 220 may be disposed within the syringe body 205. In some embodiments, the vacuum chamber 220 may be bounded by a distal wall 240 and a proximal thumb piece 260. In some embodiments, at least a portion of the vacuum chamber 220 may contain air that is pressurized to a pressure at or above standard atmospheric air pressure at sea level, as described in greater detail herein. In other embodiments, at least a portion of the vacuum chamber 220 may contain air that is pressurized to a pressure below standard atmospheric air pressure at sea level, as described in greater detail herein.

In various embodiments, the first plunger 225 may be mechanically coupled via a piston 255 to the second plunger 250. The first plunger 225 may generally be disposed at a location inside the syringe body 205, as previously described herein, and further disposed at a location that is distal to the vacuum chamber 220. In some embodiments, the positioning of the first plunger 225 and the vacuum chamber 220 may define a medial compartment 285 therebetween. Particularly, the medial compartment 285 may be formed between the proximal surface of the first plunger 225 and the distal surface of the distal wall 240. In some embodiments, the piston 255 may traverse the medial compartment 285 and extend into the vacuum chamber 220 through the distal wall 240. In some embodiments, the piston 255 may be attached by any means of attachment to the first plunger 225 and/or the second plunger 250. In some embodiments, the piston 255 may be molded as a portion of the first plunger 225 and/or the second plunger 250. In some embodiments, the piston 255 may be detachable from the first plunger 225 and/or the second plunger 250. The ability to detach the piston 255 from the plungers 225, 250 may allow for the piston to be used with varying plungers, thereby increasing compatibility with a wide range of syringes of different sizes and shapes, lowering operating costs, lowering manufacturing costs, enabling the use pre-filled syringes, and/or the like.

In various embodiments, the second plunger 250 may be located within the vacuum chamber 220. As in the embodiments depicted herein with respect to FIGS. 1A-1C, the second plunger 250 may be configured to form an airtight seal against an interior surface of the vacuum chamber 220, thereby dividing the vacuum chamber into two compartments. A distal volume compartment 265 may be created by the space between a distal surface of the second plunger 250 and the distal wall 240 of the vacuum chamber 220. A proximal volume compartment 270 may be created by the space between a proximal surface of the second plunger 250 and a distal surface of the thumb piece 260.

In various embodiments, a second seal 245 may be positioned within the distal wall 240 around the piston 255 to form an airtight seal around the piston. In some embodiments, the second seal 245 may prevent air from entering and/or escaping from the distal volume compartment 265 when the piston 255 is actuated. In some embodiments, the distal volume compartment 265 may be sealed and/or evacuated before the syringe 200 is used.

In optional embodiments, the vacuum chamber 220 may include a vent 235. The vent 235 may generally be an opening within the vacuum chamber 220 configured to allow fluid communication of air between an area outside the syringe body 205 and the proximal volume compartment 270. The vent 235 may be further configured to equalize air pressure within the proximal volume compartment 270 with the outside air pressure, as described in greater detail herein. In some embodiments, the outside air pressure may be about 14.7 psi, or standard atmospheric pressure at sea level.

Figure 2B:
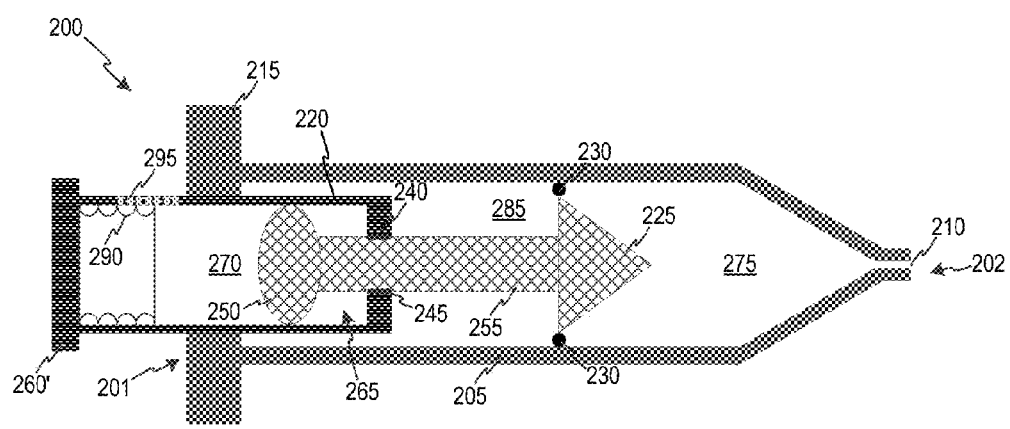
FIG. 2B depicts a side view of an alternative syringe having a screw-on thumb piece according to an embodiment.

As depicted in FIG. 2B, a movable thumb piece 260' may be used instead of a vent according to some embodiments. The movable thumb piece 260' may be moved generally distally and/or proximally by any means of movement, and is not limited by this disclosure. By way of example only, the movable thumb piece 260' in the present embodiment may contain a plurality of threads 290 that allow the thumb piece to be screwed into the vacuum chamber 220. In some embodiments, the thumb piece 260' may be screwed over the vacuum chamber 220. In other embodiments, the thumb piece 260' may be screwed inside the vacuum chamber 220. The thumb piece 260' may be screwed into a specific depth to obtain a desired pressure inside the proximal volume compartment 270, as will be described in greater detail herein. To aid in determining the pressure inside the proximal volume compartment 270 a guide 295 may be located on the syringe 200 to aid a user in determining where to position the thumb piece 260'. For example, the guide 295 may be a plurality of hash marks printed on an outside surface of the vacuum chamber 220, wherein each hash mark is labeled with the pressure that will be achieved by moving the thumb piece 260' to that hash mark. In some embodiments, the thumb piece 260 may incorporate a display that indicates the amount of adjusted pressure inside the proximal volume chamber 270.

In various embodiments, the syringe 200 may further include any number of shock absorbing devices (not shown). Specific examples of shock absorbing devices may include, for example, springs, air cushions, absorbing materials, and/or the like. The shock absorbing devices may generally function to ensure a smooth distribution of fluid out of the tip 210 at a constant rate that acts supplementary to the driving force cause by the difference in pressure, as described in greater detail herein.

Figure 3A:
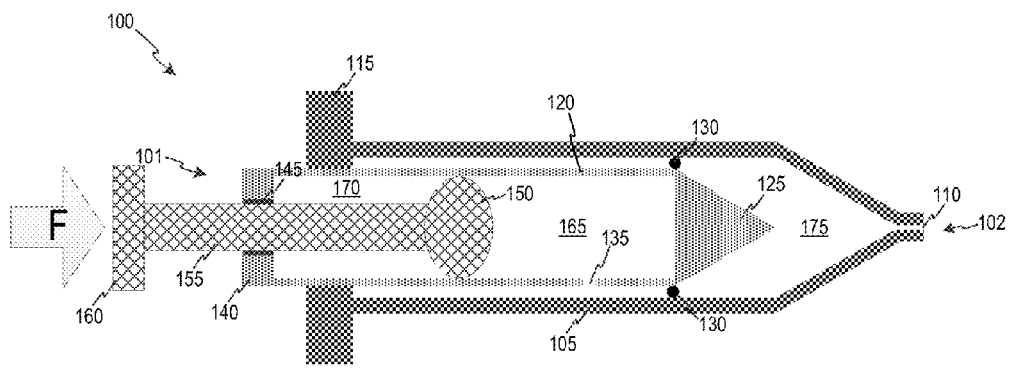
FIGS. 3A-3B depict movement of the various components of the syringe depicted in FIG. 1A according to an embodiment.
Figure 3B:
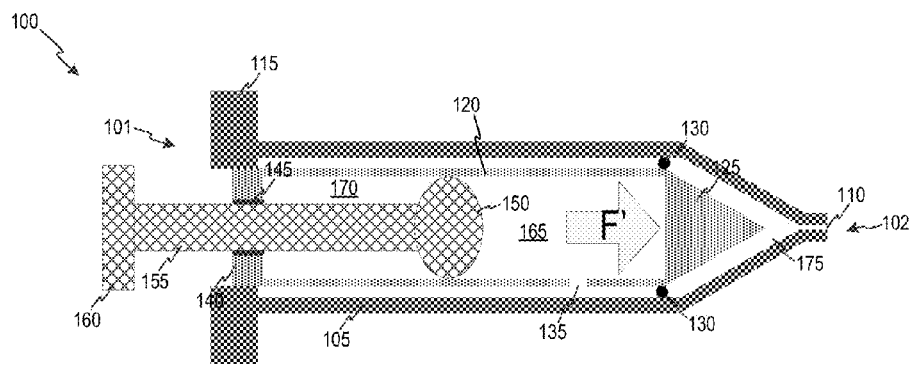

FIGS. 3A-3B depict movement of the various components of the syringe 100 depicted in FIGS. 1A-1C according to an embodiment. More particularly, FIG. 3A depicts an initial state of the syringe 100. As previously described herein, a force F may be applied to the thumb piece 160 to force the piston 155 in a distal direction into the syringe body 105. As a result, the piston 155 may mechanically force the second plunger 150 to move in a distal direction within the vacuum chamber 120.

As described in greater detail herein, the second seal 145 and the second plunger 150 may be configured to prevent air from entering the proximal volume compartment 170. In addition, the movement of the second plunger 150 in a distal direction may increase the volume of the proximal volume compartment 170. In some instances, this combination may result in a decrease in pressure in the proximal volume compartment 170 where the proximal volume compartment has a pressure greater than or equal to zero. However, in instances where the proximal volume compartment 170 is a vacuum (thereby having a zero pressure), this combination will not change the pressure within the proximal volume compartment 170. This is due to the ideal gas law, which is represented by Equation (1):

$$PV = nRT \tag{1}$$

where P is the pressure of the gas, V is the volume of the gas, n is the amount of substance of gas (also known as number of moles), T is the temperature of the gas and R is the ideal, or universal, gas constant, equal to the product of the Boltzmann constant and the Avogadro constant. To compare different volumes, Equation (1) can be written to reflect the different volumes as follows: $P_1V_1=nR_1T_1$ and $P_2V_2=nR_2T_2$. If $P_1$ and $P_2$ are both zero because of the vacuum (zero pressure), then a change in either volume $V_1$, $V_2$ won't change the results.

Furthermore, the pressure can be written as a function of force, as represented by Equation (2):

$$\Delta P = \frac{F}{A} \tag{2}$$

where ΔP is the change in pressure, F is the normal force, and A is the area of the surface on contact. Thus, in an illustrative example, if the pressure P is zero (0 psi), such as in a vacuum, then according to Equation (1), the pressure will not change when other variables change, such as, for example, the volume V. Since the pressure remains the same, the force F that is exerted by the pressure will also remain constant according to Equation (2), which allows for a smooth distribution of the fluid from within the delivery volume 175.

Similarly, the movement of the second plunger 150 in a distal direction may decrease the volume of the distal volume compartment 165. However, due to the location of the vent 135 (or in some embodiments, the bore 180), the pressure of the distal volume compartment may equalize with the outside air pressure (i.e., moving towards about 14.7 psi). As a result the force F may be active on the second plunger 150 due to the unequal pressure between the pressure of the distal volume compartment 165 and the pressure of the proximal volume compartment 170. In some embodiments, the pressure of the distal volume compartment 165 may be greater than the pressure of the proximal volume compartment 170. In other embodiments, such as those where it is desired to add fluid to the syringe 100, the pressure of the distal volume compartment 165 may be less than the pressure of the proximal volume compartment 170. In some embodiments, to ensure that the proximal volume compartment has a lower pressure than the distal volume compartment 165, the proximal volume compartment may be pre-evacuated prior to movement of the piston 155. The pre-evacuation process may be completed, for example, by attaching a vacuum pump or the like to the proximal volume compartment 170 through a sealable valve and port (not shown).

In various embodiments, because of the unequal pressure between the distal volume compartment 165 and the proximal volume compartment 170, a driving force F' may be active on the vacuum chamber 120. However, since the user may maintain force on the thumb piece 160 to keep it in a depressed state, the second plunger 150 may be fixed relative to the syringe body 105. Accordingly, the pressure difference between the distal volume compartment 165 and the proximal volume compartment 170 may force the vacuum chamber 120 to shift in the distal direction, thereby driving the first plunger 125 in a distal direction towards the distal end 102 of the syringe body 105. The resulting motion of the first plunger 125 may reduce the delivery volume 175, causing the fluid in the delivery volume to exit out the tip 110 at a steady rate. Those skilled in the art may appreciate that the driving force F' on the first plunger 125 may be due to the pressure difference developed between the proximal volume compartment 170 and the distal volume compartment 165, and may not depend on the user's force on the thumb piece 160. Those skilled in the art may also appreciate that the driving force F' on the first plunger 125 may not be due to the position of the second plunger 150 relative to the vacuum chamber 120 and/ or the syringe body 105, as long as the second plunger is not located at the proximal end 101 or the distal end 102 of the syringe body. Furthermore, the driving force F' on the first plunger 125 may not be due to the velocity of the second plunger 150 in moving towards the distal end 102 of the syringe body 105 provided that there is only a small amount of friction between the second plunger and the vacuum chamber 120. Accordingly, the rate of motion of the first plunger 125 may be smooth and may not reflect any possible unsteady movement from the user. Furthermore, the rate of delivery of the fluid from the delivery volume 175 may be adjusted by the user prior to applying force on the thumb piece 160 by increasing or decreasing the pressure of the distal volume compartment 165, as described in greater detail herein.

Figure 4A:
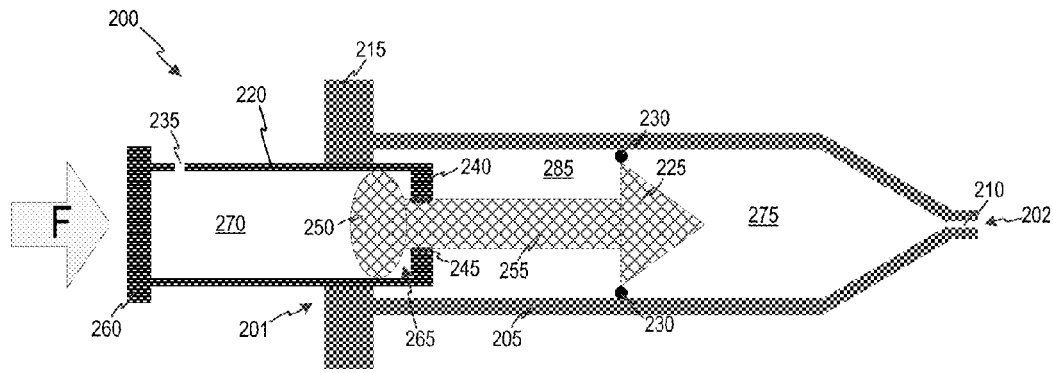
FIGS. 4A-4C depict movement of the various components of the syringe depicted in FIG. 2A according to an embodiment.
Figure 4B:
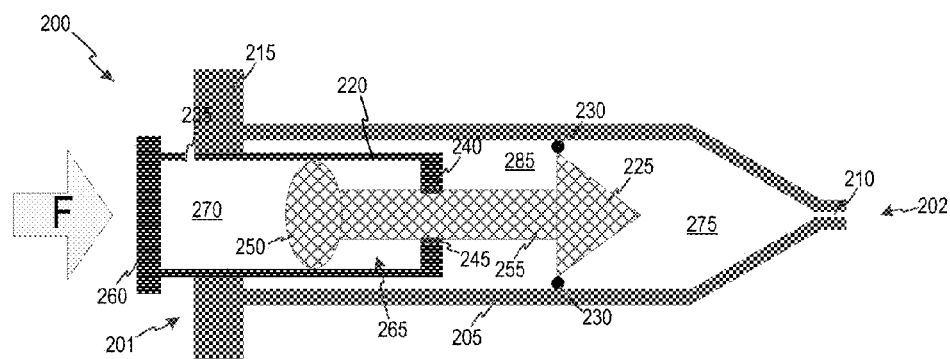
Figure 4C:
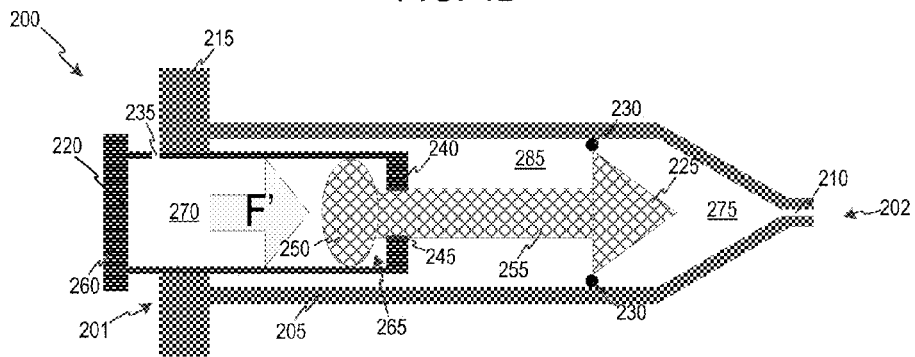

FIGS. 4A-4C depict the effect on the syringe of FIG. 2A when a force F is applied to the thumb piece 260 according to various embodiments. In some embodiments, the force F may cause the thumb piece 260 to move in a generally distal direction. This movement of the thumb piece 260 may cause the vacuum chamber 220 to also travel in a generally distal direction within the syringe body 205. In some embodiments, the various volume compartments 265, 270 may change volume as a result of the movement while the pressure remains the same (i.e., about 14.7 psi in the proximal volume compartment and zero in the distal volume compartment), as previously described herein. In some embodiments, the force F applied to the thumb piece 260 may cause the vacuum chamber 220 to move relative to the second plunger 250. The movement of the vacuum chamber 220 may therefore result in an increase in the volume of the distal volume compartment 265 and a decrease in volume of the proximal volume compartment 270. In various embodiments, a driving force F' that pushes the first plunger 225 towards the distal end 202 of the syringe body 205 may result from the difference of pressure of the proximal volume compartment 270 (where the pressure is at or near atmospheric pressure, or about 14.7 psi) and the distal volume compartment 265 (where the pressure is zero) as described herein. Accordingly, if a user of the syringe 200 provides a sharp force on the thumb piece 260, it will have no effect on the rate of ejection of fluid from the tip 210 because the difference in pressures in the distal volume compartment 265 and the proximal volume compartment 270 will continue to remain the same, even with the distal volume compartment increasing in volume. In addition, if a faster rate of ejection of fluid from the tip 210 is desired, the vent 235 can be covered with a valve or a user's finger while a force is exacted upon the thumb piece 260 to increase the pressure of the proximal volume compartment 270 and alter the driving force F' accordingly.

Figure 5A:
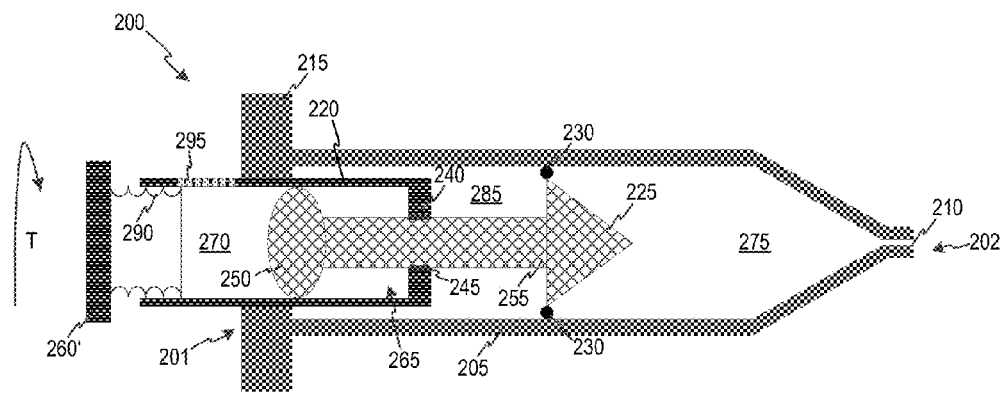
FIGS. 5A-5C depict movement of the various components of the syringe depicted in FIG. 2B according to an embodiment.
Figure 5B:
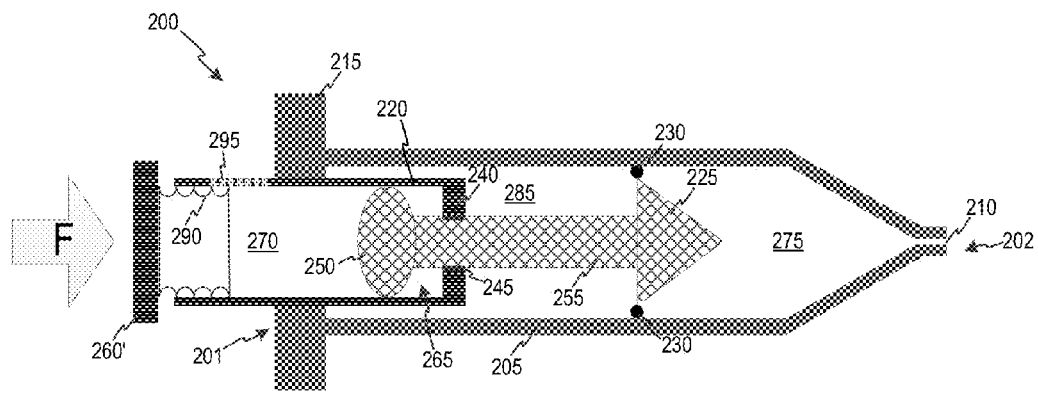
Figure 5C:
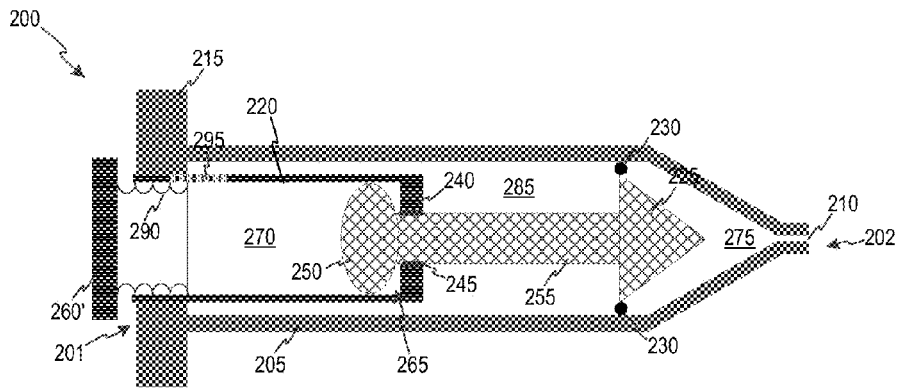

FIGS. 5A-5C depict the effect on the syringe of FIG. 2B when a force F is applied to the thumb piece 260' according to various embodiments. The movement of the various components of the syringe 200 is substantially the same as previously described herein with respect to FIGS. 4A-4C; however, instead of regulating the pressure of the proximal volume compartment 270 with a vent to increase the rate of distribution of fluid, the thumb piece 260' may be moved to adjust the pressure of the proximal volume compartment. For example, the thumb piece 260' may be moved in a proximal direction to decrease the pressure of the proximal volume compartment 270. Similarly, the thumb piece 260' may be moved in a distal direction to increase the pressure of the proximal volume compartment 270. In some embodiments, the thumb piece 260' may be moved in either direction by twisting the thumb piece in a clockwise direction T or in a counterclockwise direction (not shown). In some embodiments, adjusting the thumb piece 260' to decrease the pressure in the proximal volume compartment 270 may decrease the difference in pressure between the proximal volume compartment and the distal volume compartment 265, thereby causing the force on the second plunger 250 to decrease, which may cause a slower movement of the second plunger in the distal direction. Similarly, in some embodiments, adjusting the thumb piece 260' to increase the pressure in the proximal volume compartment 270 may increase the difference in pressure between the proximal volume compartment and the distal volume compartment 265, thereby causing the force on the second plunger 250 to increase, which may cause a faster movement of the second plunger in the distal direction.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A syringe system comprising:
    a syringe body comprising a hollow lumen and a distal end, the syringe body being configured to house a fluid therein;
    a vacuum chamber disposed within the hollow lumen of the syringe body;
    a first plunger connected to a distal portion of the vacuum chamber within the hollow lumen of the syringe body, the first plunger forming a first seal against an inner surface of the syringe body and defining a fluid delivery volume between the first plunger and the distal end of the syringe body;
    a second plunger disposed within the vacuum chamber, the second plunger forming a second seal against an inner surface of the vacuum chamber and defining a proximal volume compartment and a distal volume compartment within the vacuum chamber;
    a vent within the distal volume compartment of the vacuum chamber, wherein the vent is configured to allow communication of air between an area outside the syringe system and the distal volume compartment; and
    a piston affixed to the second plunger and extending proximally out of the vacuum chamber, the piston configured to move the second plunger within the vacuum chamber, thereby altering a volume of the proximal volume compartment and a volume of the distal volume compartment.

2. The syringe system of claim 1, wherein the vent comprises a bore extending therethrough the piston and the second plunger, the bore configured to allow communication of air between an area outside the syringe system and the distal volume compartment.

3. The syringe system of claim 2, further comprising a valve configured to regulate an amount of the air communicated between the area outside the syringe system and the distal volume compartment.

4. The syringe system of claim 1, wherein the vent comprises a side vent extending through a wall in the distal volume compartment of the vacuum chamber, wherein the side vent is configured to allow communication of air between an area outside the syringe system and the distal volume compartment.

5. The syringe system of claim 1, further comprising a tip at the distal end of the syringe body, wherein the tip is configured to allow fluid from the fluid delivery volume to pass therethrough upon movement of the first plunger in a substantially distal direction.

6. The syringe system of claim 5, wherein the tip is further configured to attach to one or more tubes, needles, or nozzles for delivery of the fluid to a patient.

7. The syringe system of claim 1, wherein the piston extends proximally out of the vacuum chamber through a proximal wall, forming a third seal between the piston and the proximal wall.

8. The syringe system of claim 1, wherein a force exacted upon the piston in a substantially distal direction is configured to cause the second plunger to move distally within the vacuum chamber, thereby increasing the volume of the proximal volume compartment and decreasing the volume of the distal volume compartment, creating a pressure difference between the proximal volume compartment and the distal volume compartment, which causes the vacuum chamber and the first plunger to move in a distal direction, thereby expelling the fluid located in the fluid delivery volume through a tip at the distal end of the syringe body.

9. A syringe system comprising:
a syringe body comprising a hollow lumen and a distal end, the syringe body being configured to house a fluid therein;
a vacuum chamber at least partially disposed within the hollow lumen of the syringe body;
a first plunger disposed distally to the vacuum chamber within the hollow lumen of the syringe body, the first plunger forming a seal against an inner surface of the syringe body and defining a fluid delivery volume between the first plunger and the distal end of the syringe body;
a second plunger slidably disposed within the vacuum chamber, the second plunger defining a proximal volume compartment and a distal volume compartment within the vacuum chamber;
a side vent extending through a wall in the proximal volume compartment of the vacuum chamber, wherein the side vent is configured to allow communication of air between an area outside the syringe system and the proximal volume compartment; and
a piston extending distally out of the vacuum chamber and connected to the first plunger and the second plunger, the piston configured to move the second plunger within the vacuum chamber and the first plunger within the syringe body,
wherein a force exacted upon the vacuum chamber in a substantially distal direction is configured to cause the vacuum chamber to move distally within the syringe body, thereby decreasing the volume of the proximal volume compartment and increasing the volume of the distal volume compartment, creating a pressure difference between the proximal volume compartment and the distal volume compartment, which causes the second plunger, the piston, and the first plunger to move in a distal direction, thereby expelling the fluid located in the fluid delivery volume out of a tip in the distal end of the syringe body.

10. The syringe system of claim 9, further comprising a tip at the distal end of the syringe body, wherein the tip is configured to allow fluid from the fluid delivery volume to pass therethrough upon movement of the first plunger in a substantially distal direction.

11. The syringe system of claim 10, wherein the tip is further configured to attach to one or more tubes, needles, or nozzles for delivery of the fluid to a patient.

12. A syringe system comprising:
a syringe body comprising a hollow lumen and a distal end having a tip, the syringe body being configured to house a fluid therein;
a vacuum chamber at least partially disposed within the hollow lumen of the syringe body;
a first plunger disposed distally to the vacuum chamber within the hollow lumen of the syringe body, the first plunger forming a seal against an inner surface of the syringe body and defining a fluid delivery volume between the first plunger and the distal end of the syringe body;
a second plunger disposed within the vacuum chamber, the second plunger defining a proximal volume compartment and a distal volume compartment within the vacuum chamber;
a piston extending distally out of the vacuum chamber and connected to the first plunger and the second plunger, wherein the piston is configured to move the second plunger within the vacuum chamber and the first plunger within the syringe body; and
a thumb piece removably attached to a proximal portion of the vacuum chamber, wherein the thumb piece is configured to provide a surface for a user to apply a force in a substantially distal direction, and wherein the thumb piece is further configured to increase and decrease a volume of the proximal volume compartment.

13. The syringe system of claim 12, wherein the thumb piece is configured to increase and decrease the volume of the proximal volume compartment by screwing into at least a portion of the vacuum chamber.

14. The syringe system of claim 12, wherein the thumb piece is configured to move in a distal direction, wherein the vacuum chamber is configured to move distally within the syringe body in response to the thumb piece moving in a distal direction, wherein the second plunger, the piston, and the first plunger are configured to move in a distal direction in response to the vacuum chamber moving distally within the syringe body.

15. A syringe system comprising:
a syringe body comprising a hollow lumen and a distal end, the syringe body being configured to house a fluid therein;
a vacuum chamber at least partially disposed within the hollow lumen of the syringe body;
a first plunger disposed distally to the vacuum chamber within the hollow lumen of the syringe body, the first plunger forming a seal against an inner surface of the syringe body and defining a fluid delivery volume between the first plunger and the distal end of the syringe body;
a second plunger disposed within the vacuum chamber, the second plunger defining a proximal volume compartment and a distal volume compartment within the vacuum chamber;
a thumb piece configured to screw into a proximal portion of the vacuum chamber, wherein the thumb piece is configured to increase and decrease a pressure of the proximal volume compartment; and
a piston extending distally out of the vacuum chamber and connected to the first plunger and the second plunger, wherein the piston is configured to move the second plunger within the vacuum chamber and the first plunger within the syringe body.

16. The syringe system of claim 15, further comprising a guide on an outside surface of the vacuum chamber, wherein the guide is configured to assist a user of the syringe system to screw the thumb piece to a desired depth in the vacuum chamber to ensure a desired volume of the proximal volume compartment.

17. The syringe system of claim 15, wherein the thumb piece is further configured to increase and decrease a flow rate of the fluid out of the syringe system.

* * * * *

UNITED STATES PATENT AND TRADEMARK OFFICE
CERTIFICATE OF CORRECTION

| | | |
|---|---|---|
| PATENT NO. | : 9,101,713 B2 | Page 1 of 1 |
| APPLICATION NO. | : 13/797959 | |
| DATED | : August 11, 2015 | |
| INVENTOR(S) | : Cowan et al. | |

It is certified that error appears in the above-identified patent and that said Letters Patent is hereby corrected as shown below:

IN THE SPECIFICATION:
Column 5, Line 6, delete "chamber 165" and insert -- chamber 120 --, therefor.
Column 5, Line 9, delete "chamber 165" and insert -- chamber 120 --, therefor.

Signed and Sealed this
Fifteenth Day of March, 2016

Michelle K. Lee
*Director of the United States Patent and Trademark Office*